US009168321B2

United States Patent
Oestergaard et al.

(10) Patent No.: US 9,168,321 B2
(45) Date of Patent: Oct. 27, 2015

(54) TOROIDAL-SHAPED TREATMENT DEVICE FOR DISINFECTING A FLUID SUCH AS AIR OR WATER

(71) Applicant: SYDDANSK UNIVERSITET, Odense M (DK)

(72) Inventors: John Erland Oestergaard, Odense M (DK); Thomas Rubaek, Odense C (DK)

(73) Assignee: SYDDANSK UNIVERSITET, Odense M (DK)

( * ) Notice: Subject to any disclaimer, the term of this patent is extended or adjusted under 35 U.S.C. 154(b) by 0 days.

(21) Appl. No.: 14/355,650

(22) PCT Filed: Oct. 31, 2012

(86) PCT No.: PCT/DK2012/050401
§ 371 (c)(1),
(2) Date: May 1, 2014

(87) PCT Pub. No.: WO2013/064154
PCT Pub. Date: May 10, 2013

(65) Prior Publication Data
US 2014/0271353 A1 Sep. 18, 2014

(30) Foreign Application Priority Data

Nov. 2, 2011 (DK) .............................. 2011 00851

(51) Int. Cl.
| A61L 2/00 | (2006.01) |
| G01N 23/00 | (2006.01) |
| A61N 5/00 | (2006.01) |
| B01D 17/06 | (2006.01) |
| A61L 2/10 | (2006.01) |

(Continued)

(52) U.S. Cl.
CPC . *A61L 2/10* (2013.01); *B05D 3/067* (2013.01); *C02F 1/325* (2013.01); *C02F 2103/008* (2013.01); *C02F 2201/009* (2013.01); *C02F 2201/3222* (2013.01); *C02F 2201/3228* (2013.01); *C02F 2305/10* (2013.01)

(58) Field of Classification Search
CPC ............... A61L 2/00; C02F 1/00; C02F 1/30; C02F 1/32; C02F 1/325; C02F 1/36
USPC ............... 422/24; 210/748.01, 748.02, 748.1, 210/748.11; 250/432 R, 453.11, 455.11, 250/492.1
See application file for complete search history.

(56) References Cited

U.S. PATENT DOCUMENTS

2009/0272320 A1 11/2009 Wakalopulos
2010/0237254 A1* 9/2010 Mason et al. ................. 250/435

FOREIGN PATENT DOCUMENTS

| JP | 2011-16074 | * | 1/2011 | ............... B01J 21/06 |
| KR | 10-2011-0012488 | | 2/2011 | |

(Continued)

OTHER PUBLICATIONS

Japanese Patent Office English Translation of the Detaled section of JP 2011-16074.*

(Continued)

*Primary Examiner* — Monzer R Chorbaji
(74) *Attorney, Agent, or Firm* — Merchant & Gould P.C.

(57) ABSTRACT

There is provided a treatment device for disinfecting a fluid being configured as a conduit for conveying a flow of fluid to be treated, said device being toroidal-shaped with an inner concave parabolic surface, wherein the device is provided with apertures extending from the outer to the inner surface of the toroidal-shaped device; one or more UV LED(s) provided in the apertures thereby enabling emitted light to be transmitted through the apertures into the interior part of the device for disinfecting said fluid; a power source for powering the UV LEDs, wherein the inner surface is made from a light reflecting material, and the apertures are sealed in the ends extending into the interior part of the device by a UV-transparent material.

13 Claims, 4 Drawing Sheets

(51) Int. Cl.
　　*C02F 1/32*　　(2006.01)
　　*B05D 3/06*　　(2006.01)
　　*C02F 103/00*　(2006.01)

(56) References Cited

FOREIGN PATENT DOCUMENTS

| WO | WO 02/12127 | 2/2002 |
| WO | WO 2007/113537 | 10/2007 |
| WO | WO 2010/046906 | 4/2010 |
| WO | WO 2010/071814 | 6/2010 |

OTHER PUBLICATIONS

Japanese Patent Office English illustration of the drawings in JP 2011-16074.*
International Search Report from International Application No. PCT/DK2012/050401 mailed Jan. 28, 2013.

* cited by examiner

TOROIDAL-SHAPED TREATMENT DEVICE FOR DISINFECTING A FLUID SUCH AS AIR OR WATER

This application is a National Stage Application of PCT/DK2012/050401, filed 31 Oct. 2012, which claims benefit of Serial No. PA 2011 00851, filed 2, Nov. 2011, in Denmark and which applications are incorporated herein by reference. To the extent appropriate, a claim of priority is made to each of the above disclosed applications.

FIELD OF THE INVENTION

The present invention relates to a treatment device and more particularly treatment device for disinfecting a fluid such as air or water.

BACKGROUND OF THE INVENTION

Sterilization technology is absolutely essential for our daily life. For example, it is used for water and sewerage system, foods, and medicine. Methods widely used for sterilization use drug, heating, ultraviolet (UV) radiation, and ozone. Chlorine is used extensively in sterilization because of its easiness and low cost. Using chlorine has some adverse effects such as alteration of quality of the target. Also it is bad for environment discharge water sterilized by drug to rivers and oceans. Conventional methods for UV sterilization use UV lamps. These are used to sterilize workspaces and tools used in biology laboratories and medical facilities. Low pressure mercury-vapor lamps emit 254, nm wavelength of UV which coincides very well with peaks of the germicidal effectiveness curve (i.e., effectiveness for UV absorption by DNA). Low pressure mercury-vapor lamps contain mercury and it has harmful effects to the environment and human body.

There are many systems that use ultraviolet light. Some systems are designed to generate effects such as fluorescing effects while other systems are used for the purification of objects, liquids and vapor.

Water purification systems are in great demand for industrial, home, portable, and other uses. These systems are designed to purify a predetermined quantity of water before dispensing for consumption or other use. There are many techniques or methods used to purify water. Usually, multiple techniques are employed within one purification device. Filters are generally used to remove particulates from the water while ultra-violet light is used to disinfect the water. The disinfection process may involve passing water through a clear tube while passing ultraviolet light through the tube simultaneously. The ultraviolet radiation is used to eliminate most bacteria and viruses.

UV light disinfects water by permanently deactivating organisms such as bacteria, spores, moulds, viruses or the like. Light having wavelengths between 200, nm and 300 nm, also known as UVC, is known to be responsible for this effect. This application of UV sterilisation in aquatic environments such as ponds or aquariums is also known.

However, UV lamps and tubes have relatively high power consumption. UV lamps and tubes also degrade over time and eventually become ineffective for water treatment making replacement necessary. This adds significantly to the costs of UV water treatment, both because of the relatively high cost of the new tubes, and because of the frequency of replacement. Furthermore, UV degradation is not immediately obvious to an observer. Hence, treatment lamps and tubes are often used for a long time after they become ineffective.

Although the sterilization technology using UV is a traditional method, development of efficient and low cost sterilization equipment is still lacking.

Also air contamination, particularly indoor air contamination, contributes to human health complications. Specifically, airborne chemical and/or biological contaminants, particularly when present in poorly ventilated areas, cause a wide variety of human illnesses. Biological contaminants include bacteria, fungi, fungi spores, protozoa, viruses, algae, pollen, various antigenic agents, and the like, and are known to cause such health complications as pneumonia, fever, mycotoxicosis, various infections, asthma and the like. Prior art air sterilization devices suffer from a number of problems. First, the devices are large and consume significant amounts of useable space in an office or home environment. Second, though they may provide a means for reducing airborne contaminants, they do not address the odors that may be present in the areas of intended use. In addition, the prior art devices are very inefficient. More often than not, they require an associated volume of air in the area of intended use to be recirculated multiple times through the device in order for the contaminants to be effectively removed.

WO2010071814A1, discloses a system for disinfecting a fluid. The system includes a flow cell with inlet and outlet ports, configured to communicate a fluid containing a biological contaminant from the inlet ports to the outlet ports through an interior portion thereof. The flow cell wall is provided with apertures and point radiation sources are disposed in these apertures. The point radiation sources are described to be UV optical sources, deep-UV optical sources, semiconductor optical sources, and/or LED optical sources. They are operable for delivering radiation to the biological contaminant. The interior surface of the flow cell reflects the radiation delivered by the point radiation source(s) such that a radiation intensity is uniform throughout the interior portion of the flow cell. The flow cell can be an integrating sphere or an integrating ellipsoid.

WO2007113537A1, discloses a treatment apparatus for at least partially disinfecting a fluid such as water comprising a pipe for conveying a flow of fluid to be treated, a series of ultraviolet (UV) light emitting diodes (LEDs) for emission of UV light into the fluid, and a control circuit for controlling operation of the LEDs. The pipe has apertures extending from the outer surface to the inner surface of the pipe and the UV LEDs are placed in the apertures. The aperture are sealed for fluid impermeability such that the fluid flowing in the tube, in operation, does not leak out of the pipe through wall. Electrical circuitry for operation of the LEDs is located on a flexible printed circuit board (PCB) wrapped cylindrically around the pipe. The apparatus also includes sensors which can for example monitor the level of UV or natural light passing through the fluid.

The prior art does not utilize UV LED point radiation sources emitting light through apertures sealed in the ends with a UV transparent material, and there is no indication that the flow cell is toroidal-shaped with an inner concave parabolic surface.

It is an object of the present invention to overcome one or more of the aforementioned problems in removing and/or generally reducing the presence of air or water borne contaminants in an efficient manner. In particular, there is a need for a flow cell with improved disinfection of a fluid to be treated.

SUMMARY OF THE INVENTION

This object is achieved by means of a treatment device for disinfecting a fluid, such as air or water, in accordance with the present invention.

Specifically the present invention provides a treatment device (1) for disinfecting a fluid, said device configured as a conduit for conveying a flow of fluid to be treated, said device (1) being toroidal-shaped with an inner concave parabolic surface (2), wherein:

the device (1) is provided with apertures (3) extending from the outer to the inner surface of the toroidal-shaped device (1);

one or more UV LED(s) (4) provided in the apertures thereby enabling emitted light to be transmitted through the apertures (3) into the interior part of the device (1) for disinfecting said fluid; and a power source for powering the UV LEDs (4), wherein the inner surface (2) is made from a light reflecting material, and the apertures (3) are sealed in the ends extending into the interior part of the device by a UV-transparent material.

The present inventors have surprisingly found that when the device (1) further comprises one or more ultrasound transducers provided in the apertures (3) or on the outer surface of the device (1) so as to direct ultrasound waves into the interior part of the device (1), the combined action of the UV light and the ultrasound waves act in a synergistic manner as far as disinfection is concerned. A plausible explanation is that the ultrasound disrupt the cells to be treated thereby rendering them more prone to damage from the UV light.

Preferably the LED(s) are arranged in the apertures (3) close to the interior part of the device (1). Also preferred is that the inner surface of the conduit is made from a frictionless material in order to avoid undesired deposits.

The device (1) may further comprise sensing means for sensing the light level in the fluid and generate a signal in dependence thereon and wherein said power source is operable to control energising of said one or more LED(s) in response to said signal.

In a preferred embodiment the one or more LED(s) (4) comprises a light emitting portion, and an electrical connection portion, arranged such that said light emitting portion extends into the interior part of the device (1), and said electrical connection portion is located inside the aperture (3).

Preferably the circuitry for the operation of said LED(s) is located around an external surface of the device.

More preferably said circuitry is provided on a flexible printed circuit board wrapped around said device.

The LEDs (4) are arranged in the apertures (3) such that fluid flowing in the conduit flows over a surface of each LED (4) that provides for greater treatment efficiency because of the close proximity of each LED (4) to the fluid being treated. It also has the unexpected advantage that the cooling effect of the fluid flow allows each LED (4) to be operated at above its maximum rated power. Operating the LED (4) above its maximum rated power allows a higher intensity of UV light to be produced and hence improved treatment capabilities, efficiencies.

Provision of control means configured for pulsing the LED (4) allows the or each LED (4) to be operated at a duty cycle of less than 100% thereby allowing the LED (4) to be operated above its maximum rated power for continuous operation, whilst reducing the overall power consumed, thereby providing enhanced treatment capabilities per unit power consumed. The use of a pulsed signal is also results in good treatment efficiency.

DETAILED DESCRIPTION OF THE INVENTION

Figure 1:
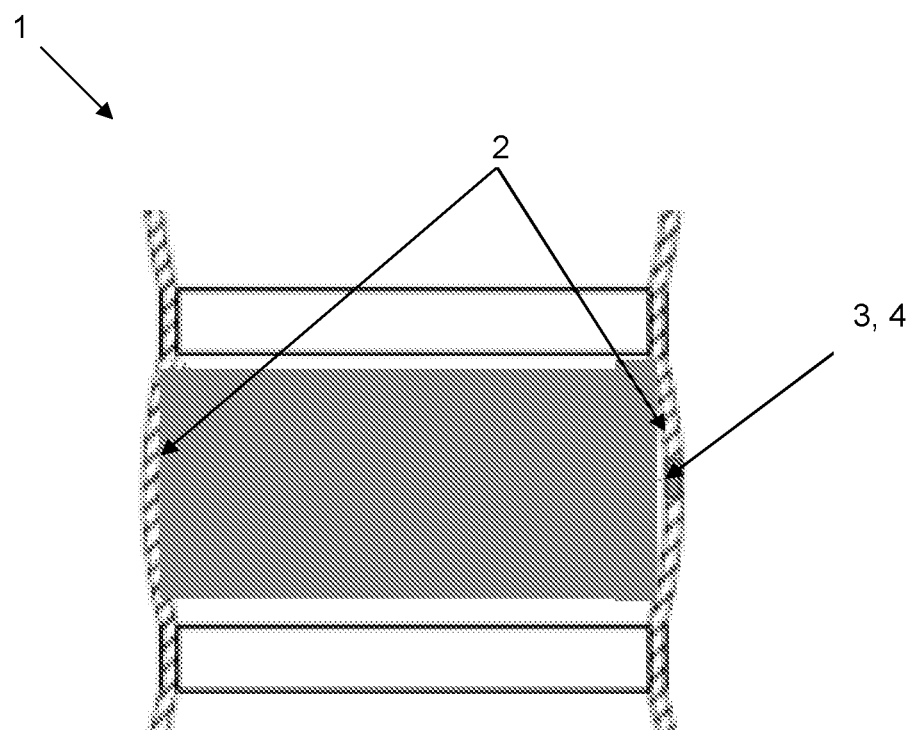
FIG. 1 is a cross-sectional view of a reflector of this invention.
Figure 3:
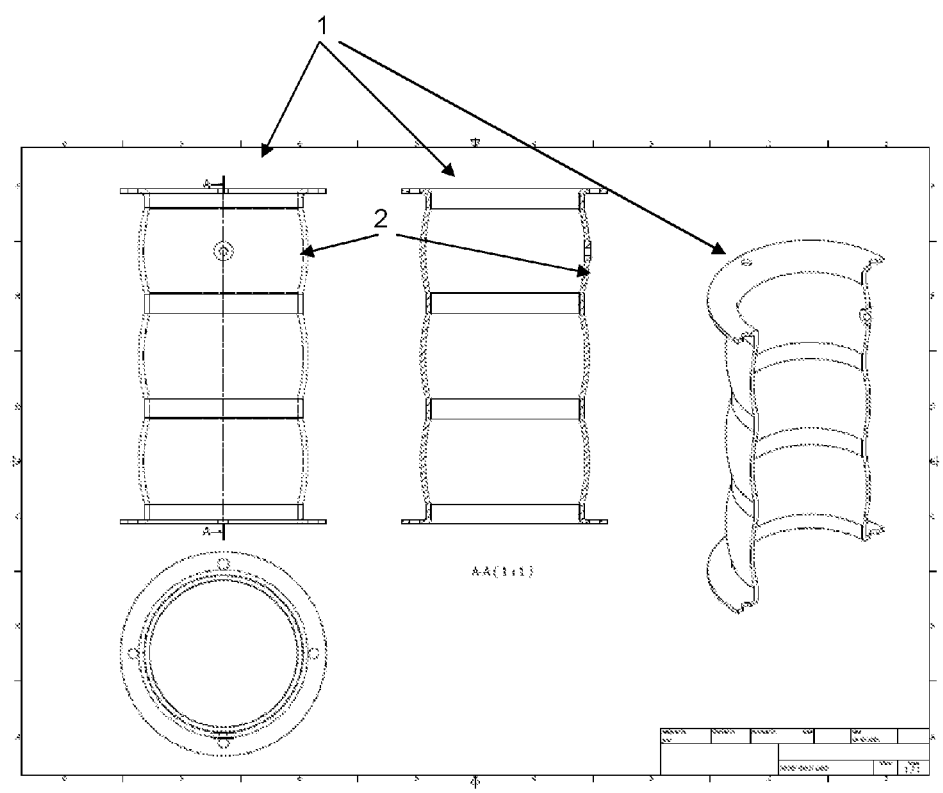
FIG. 3 shows cross-sectional views of a triple-reflector embodiment of this invention.

In FIGS. 1 and 3 treatment devices of the present invention for disinfecting water are shown. The devices (1) are toroidal-shaped with inner concave parabolic surface (2). The device is provided with apertures (3) extending from the outer to the inner surface of the toroidal-shaped device; one or more UV LED(s) (4) provided in the apertures thereby enabling emitted light to be transmitted through the apertures into the interior part of the device for disinfecting said fluid; a power source for powering the UV LEDs. The inner surface is made from a light reflecting material, and the apertures are sealed in the ends extending into the interior part of the device by a UV-transparent material.

The embodiment shown in FIG. 3 includes three toroidal-shaped devices in a row. The figures are shown for illustrative purposes only, and are not to scale. It will be appreciated that although the device is described with reference to water the apparatus may also be used for treating other fluids, including air, containing organisms or organics. It will be further appreciated that the device may be used in many applications, for example, the provision of safe drinking water or the destruction of organisms or organics for environmental applications.

Referring to FIG. 1 there is shown a section of a treatment devices of the present invention with a parabolic reflector cavity (PRC). The parabolic reflector is designed with a radius of curvature of R resulting in a focal length f of the reflector with f=R/2. The diameter of the toroidial reflector is f if the cavity is filled with air (refractive index of 1, otherwise the diameter must be compensated). A mounted LED (4) on the one side of the reflector (to the right) has preferentially an emission radius as sketched matching the reflecting surface on the other side at a distance of f. This emitter is placed in the focal point of the parabolic reflector and thus the light beam will be a parallel collimated beam after the reflector hitting the other side as such. Since this is a parabolic reflector with an incoming parallel beam it will focus the light in the focal point which happens to be at the other reflecting surface as shown in FIG. 1. From this point on this is repeated a number of times resulting in a light intensity enhancement in the cavity that can be used for e.g. optimum bacterial treatment.

Figure 2:
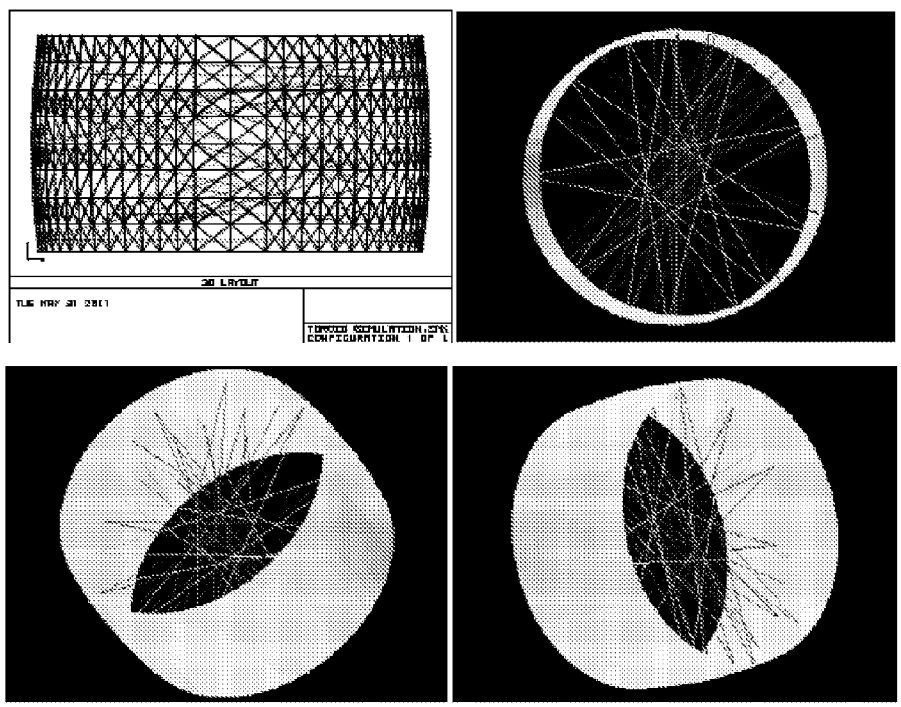
FIG. 2 is a schematic representation of the light dispersion from an LED (4) of the present invention.

Referring to FIG. 2 there is shown a simulation of light propagation in the parabolic reflector cavity of FIG. 1. Using the design principles for the PRC a realization of the PRC is simulated in the figure below. The light propagates multiple times back and forth in the cavity thereby enhancing the light intensity in the cavity for e.g. bacterial treatment.

Referring to FIG. 3 there is shown a 3section implementation of the PRC. An aperture (3) in the upper section for mounting UV LED is also shown, however, such apertures (3) can be distributed along the inner surface of each of the PRCs. For flow applications an inner UV transparent section for the liquid flow through the PRCs must be designed and included.

Figure 4:
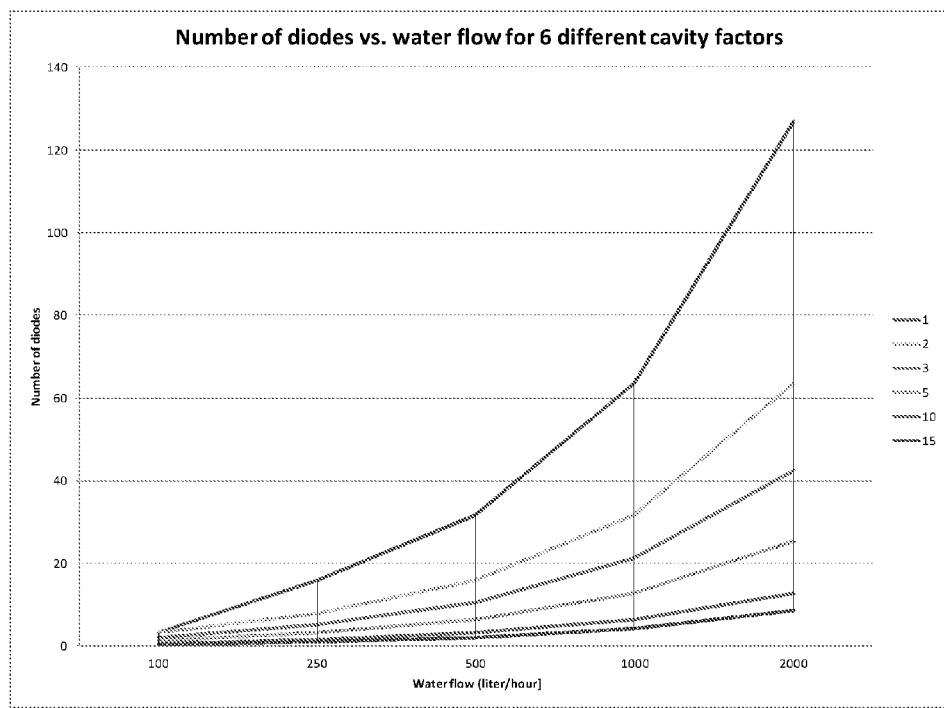
FIG. 4 shows the number of diodes in the parabolic reflector cavity versus the water flow.

Referring to FIG. 4 there is shown the number of diodes in the parabolic reflector cavity versus the water flow. The calculated reduction of diodes in the parabolic reflector cavity is here shown for an increased cavity factor from 1, to 15. The cavity factor describes how many times the light travels back and forth in the PRC. For the calculation is used realistic parameters: Reflector loss per reflection: 2%, loss in the water and acryl in the PRC: 18%, log 1, rate for removing 90% of *E. Coli*, bacteria: 30, Ws/m2, UV optical effect from LED: 5, mW. The PRC construction enables a substantial reduction in the number of diodes necessary for the functionality making the PRC a very practical construction.

The invention claimed is:

1. A treatment device for disinfecting a fluid configured as a conduit for conveying a flow of fluid to be treated, said treatment device being toroidal-shaped with an outer surface, an inner concave parabolic surface, and an inner part, wherein:
   the device is provided with apertures extending from the outer to the inner concave parabolic surface of the toroidal-shaped device;
   one or more UV LED(s) provided in the apertures thereby enabling emitted light to be transmitted through the apertures into the interior part of the device for disinfecting said fluid; and
   a power source for powering the UV LED(s),
   wherein the inner surface is made from a light reflecting material, and the apertures are sealed at ends extending into the interior part of the device (1) by a UV-transparent material.

2. The device of claim 1 further comprising one or more ultrasound transducers provided in the apertures or on the outer surface of the device so as to direct ultrasound waves into the interior part of the device.

3. The device of claim 1, wherein the LED(s) are arranged in the apertures close to the interior part of the device.

4. The device of claim 1 further comprising sensing means for sensing the light level in the fluid and generate a signal in dependence thereon and wherein said power source is operable to control energising of said one or more LED(s) in response to said signal.

5. The device of claim 1, where the one or more LED(s) comprises a light emitting portion, and a electrical connection portion, arranged such that said light emitting portion extends into the interior part of the device, and said electrical connection portion is located inside the aperture.

6. The device of claim 1, wherein circuitry for operation of said LED(s) is located around an external surface of the device.

7. The device of claim 6, wherein said circuitry is provided on a flexible printed circuit board wrapped around said device.

8. The device of claim 1, wherein the light reflecting material is titanium dioxide ($TiO_2$).

9. The device of claim 1, wherein a rotor for generating power is connected to the LED(s), said rotor being powered by the flow of fluid to be treated.

10. A method for disinfecting a water flow, the method comprising:
    (a) flowing water through a treatment device, the treatment device being toroidal-shaped with an outer surface, an inner concave parabolic surface, and an inner part, wherein:
    the device is provided with apertures extending from the outer to the inner concave parabolic surface of the toroidal-shaped device;
    one or more UV LED(s) provided in the apertures thereby enabling emitted light to be transmitted through the apertures into the interior part of the device for disinfecting said fluid; and
    a power source for powering the UV LED(s),
    wherein the inner surface is made from a light reflecting material, and the apertures are sealed at ends extending into the interior part of the device by a UV-transparent material.

11. The method according to claim 10, wherein the water flow comprises water from ship ballast tanks.

12. A method for curing coatings and paints on the surface of objects, the method comprising:
    (a) flowing the objects through a treatment device, the treatment device being toroidal-shaped with an outer surface, an inner concave parabolic surface, and an inner part, wherein:
    the device is provided with apertures extending from the outer to the inner concave parabolic surface of the toroidal-shaped device;
    one or more UV LED(s) provided in the apertures thereby enabling emitted light to be transmitted through the apertures into the interior part of the device for disinfecting said fluid; and
    a power source for powering the UV LED(s),
    wherein the inner surface is made from a light reflecting material, and the apertures are sealed at ends extending into the interior part of the device by a UV-transparent material.

13. The method of claim 12, wherein the objects have a circular surface.

* * * * *